(12) United States Patent
Borgmeier et al.

(10) Patent No.: US 7,038,082 B2
(45) Date of Patent: May 2, 2006

(54) PREPARATION OF A MULTIMETAL OXIDE MATERIAL

(75) Inventors: Frieder Borgmeier, Mannheim (DE); Klaus Joachim Müller-Engel, Stutensee (DE); Hartmut Hibst, Schriesheim (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 131 days.

(21) Appl. No.: 10/647,335

(22) Filed: Aug. 26, 2003

(65) Prior Publication Data

US 2004/0097368 A1   May 20, 2004

(30) Foreign Application Priority Data

| Oct. 17, 2002 | (DE) | ................................ 102 48 584 |
| Nov. 20, 2002 | (DE) | ................................ 102 54 278 |
| Nov. 20, 2002 | (DE) | ................................ 102 54 279 |

(51) Int. Cl.
   *B01J 29/06*   (2006.01)

(52) U.S. Cl. ................... 562/598; 562/549; 562/542; 562/311; 562/312; 562/545; 562/600; 502/305; 502/306; 502/307; 502/308; 502/310; 502/311; 502/312; 502/313; 502/315; 502/317; 502/318; 502/309; 502/321; 502/325; 502/340; 502/344; 502/353; 502/304

(58) Field of Classification Search ................ 502/305, 502/306, 307, 308, 310, 311, 312, 313, 315, 502/317, 318, 309, 321, 325, 340, 344, 353, 502/304; 562/598, 549, 542, 311, 312, 545, 562/600

See application file for complete search history.

(56) References Cited

U.S. PATENT DOCUMENTS

| 6,036,880 | A   |   | 3/2000  | Komada et al. |        |
| 6,043,185 | A   | * | 3/2000  | Cirjak et al. | 502/311 |
| 6,063,728 | A   |   | 5/2000  | Hinago et al. |        |
| 6,143,916 | A   |   | 11/2000 | Hinago et al. |        |
| 6,383,978 | B1  | * | 5/2002  | Bogan, Jr. | 502/311 |
| 6,403,525 | B1  | * | 6/2002  | Chaturvedi et al. | 502/311 |
| 6,407,031 | B1  | * | 6/2002  | Chaturvedi et al. | 502/311 |
| 6,407,280 | B1  | * | 6/2002  | Chaturvedi et al. | 558/319 |
| 6,589,907 | B1  | * | 7/2003  | Chaturvedi et al. | 502/311 |
| 6,610,629 | B1  | * | 8/2003  | Hinago et al. | 502/300 |
| 6,642,173 | B1  | * | 11/2003 | Bogan, Jr. | 502/311 |
| 6,734,136 | B1  | * | 5/2004  | Chaturvedi et al. | 502/215 |
| 2003/0187298 | A1 | * | 10/2003 | Borgmeier et al. | 562/546 |

FOREIGN PATENT DOCUMENTS

| DE | 198 35 247   | 2/1999  |
| DE | 101 18 814   | 10/2002 |
| DE | 101 19 933   | 10/2002 |
| DE | 102 48 584   | 4/2004  |
| EP | 0 895 809    | 2/1999  |
| EP | 1 192 987    | 4/2002  |
| EP | 1 254 707    | 11/2002 |
| EP | 1 254 709    | 11/2002 |
| EP | 1 254 710    | 11/2002 |
| JP | 08-057319    | 3/1996  |
| WO | WO 02/06199  | 1/2002  |
| WO | WO 02/051539 | 7/2002  |

OTHER PUBLICATIONS

H. Watanabe, et al., Applied Catalysis A: General, vol. 194-195, XP-004272252, pp. 479-485, "New Synthesis Route for Mo-V-Nb-Te Mixed Oxides Catalyst for Propane Ammoxidation", Mar. 13, 2000.

* cited by examiner

*Primary Examiner*—Christina Johnson
(74) *Attorney, Agent, or Firm*—Oblon, Spivak, McClelland, Maier & Neustadt, P.C.

(57) ABSTRACT

A process for preparing a multimetal oxide material which contains the elements Mo, V and Te and/or Sb and at least one of the elements Nb, Ti, W, Ta and Ce and if desired promoters and has a specific X-ray diffraction pattern, in which process the last process step comprises washing with acidic liquids. In addition, a multimetal oxide material obtainable in such a way is used as a catalyst for heterogeneously catalyzed gas-phase partial oxidations and/or ammoxidation of hydrocarbons.

11 Claims, 4 Drawing Sheets

PREPARATION OF A MULTIMETAL OXIDE MATERIAL

BACKGROUND OF THE INVENTION

1. Field of the Invention

The present invention relates to a process for preparing a multimetal oxide material M of the stoichiometry I $$Mo_1V_aM^1_bM^2_cM^3_dO_n \qquad (I)$$

where

M$^1$ is at least one of the elements from the group consisting of Te and Sb;

M$^2$ is at least one of the elements from the group consisting of Nb, Ti, W, Ta and Ce;

M$^3$ is at least one of the elements from the group consisting of Pb, Ni, Co, Bi, Pd, Ag, Pt, Cu, Au, Ga, Zn, Sn, In, Re, Ir, Sm, Sc, Y, Pr, Nd and Tb;

a is from 0.01 to 1, b is from >0 to 1, c is from >0 to 1, d is from >0 to 0.5 and n is a number which is determined by the valency and frequency of the elements other than oxygen in (I), whose X-ray diffraction pattern has reflections h, i and k whose peaks are at the diffraction angles (2θ) 22.2±0.5° (h), 27.3±0.5° (i) and 28.2±0.5° (k), the reflection h being the one with the strongest intensity with in the X-ray diffraction pattern and having a full width at half height (FWHH) of not more than 0.5°, the intensity $P_i$ of the reflection i and the intensity $P_k$ of the reflection k satisfying the relationship 0.65≦R≦0.85, where R is the intensity ratio defined by the formula $$R=P_i/(P_i+P_k)$$

and the FWHH of the reflection i and that of the reflection k being each ≦1°, but has no reflection with the peak position 2θ=50.0±0.3°, in which first such a multimetal oxide material M is prepared with the proviso that, in the course of the preparation of this multimetal oxide material M, no precursor multimetal oxide material of this multimetal oxide material M is washed with a liquid from the group consisting of organic acids, inorganic acids, solutions of organic acids, solutions of inorganic acids and mixtures of the abovementioned group members. The present invention also relates to the use of multimetal oxide materials M obtainable according to the invention as active material for catalysts for the heterogeneously catalyzed gas-phase partial oxidation and/or ammoxidation of saturated and/or unsaturated hydrocarbons.

2. Discussion of the Background

Multimetal oxide materials M are known (cf. for example DE-A 10248584, DE-A 10119933 and DE-A 10118814). They are suitable as catalysts for heterogeneously catalyzed partial gas-phase oxidations and/or ammoxidations of saturated and unsaturated hydrocarbons, as described, for example, in the abovementioned publications. If propane and/or propene is used as the hydrocarbon, for example, acrolein, acrylic acid and/or acrylonitrile can be produced as target compounds. These are key intermediates which are used, for example, for the preparation of polymers which can be employed, for example, as adhesives.

The preparation of multimetal oxide materials M is carried out according to the teachings of DE-A 10248584, DE-10119933 and DE-A 10118814 in a systematic manner in which first a precursor multimetal oxide material differing from a multimetal oxide material M (this term is intended to be understood as meaning very generally multimetal oxide materials which occur along the route to a multimetal oxide material M) and whose X-ray diffraction pattern has a reflection having a secondary phase at the peak position 2θ=50.0±0.3° is produced and this precursor multimetal oxide material is then washed with a liquid from the group consisting of organic acids, inorganic acids, solutions of organic acids, solutions of inorganic acids and mixtures of the abovementioned group members. The acidic washing of Mo- and V-containing multimetal oxide materials is recommended in JP-A 8-57319 also for activation reasons.

In a less systematic manner, multimetal oxide materials M are however also obtainable directly by producing a very intimate, preferably finely divided dry blend from sources (starting compounds) of their elemental constituents and then converting said dry blend by thermal treatment into an active multimetal oxide M without a wash to be carried out as described above being involved.

Example 11 of DE-A 19835247 and Example 6 of EP-A 895809 may be mentioned by way of example.

However, a disadvantage of such directly obtained multimetal oxide materials M is that the selectivity of the formation of the target compound is as a rule not completely satisfactory when they are used as catalysts for heterogeneously catalyzed partial gas-phase oxidations and/or ammoxidations of saturated and/or unsaturated hydrocarbons.

SUMMARY OF THE INVENTION

It is an object of the present invention to provide a process which substantially reduces or completely eliminates this the disadvantage of directly obtained multimetal oxide materials M.

DETAILED DESCRIPTION OF THE INVENTION

Figure 1:
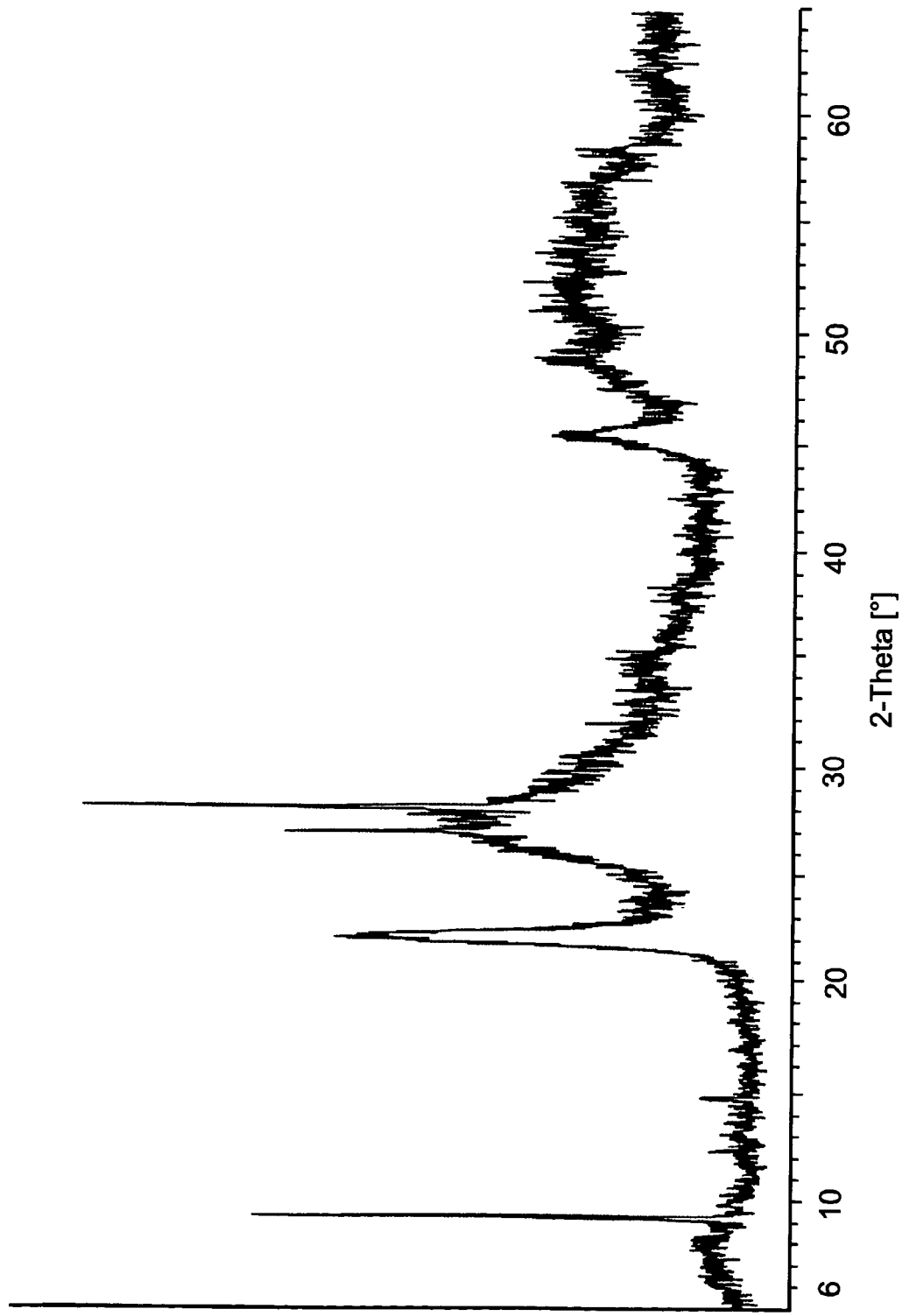
FIG. 1 shows the associated X-ray diffraction pattern of the Comparative Example prior to heating in a rotating bulb furnace.

We have found that this object is achieved by a process for preparing multimetal oxide materials M, in which first such a multimetal oxide material M is prepared with the proviso that, in the course of the preparation of this multimetal oxide material M, no precursor multimetal oxide material of this multimetal oxide material M is washed with a liquid F from the group consisting of organic acids, inorganic acids, solutions of organic acids, solutions of inorganic acids and mixtures of the abovementioned group members, wherein the multimetal oxide material M initially prepared in this manner is washed with a liquid F from the group consisting of organic acids, inorganic acids, solutions of organic acids, solutions of inorganic acids and mixtures of the abovementioned group members.

In this document, the term acid means protic Brönsted acids according to H. R. Christen, Grundlagen der allgemeinen und anorganischen Chemie, Sauerländer Verlag, 1973.

Wash liquids F suitable according to the invention are, for example, organic acids, such as oxalic acid, formic acid, acetic acid, citric acid, tartaric acid and/or solutions thereof, for example aqueous solutions thereof. Such an aqueous solution may also contain two or more of the abovementioned organic acids in solution.

Instead of water, alcohols (e.g. methanol and/or ethanol) and/or aqueous solutions thereof can also be used as solvents. Instead of said organic acids, inorganic acids, for example nitric acid, can also be used according to the invention as wash liquid F. The inorganic acids too, can be used in aqueous or other, e.g. alcoholic or aqueous alcoholic (e.g. methanolic and/or ethanolic) solution. According to the invention, an aqueous nitric acid is preferably used as wash liquid F.

Of course, a mixture of organic and inorganic acids may also be used as wash liquid F. This mixture, like all the above acids, can be used in water, alcohols (e.g. methanol or ethanol) or mixtures thereof. As a rule, the acid solutions contain from 5 to 30, frequently from 5 to 15, % by weight of acid in solution. If required, hydrogen peroxide may also be added to said acidic wash liquids F.

The novel washing is advantageously carried out at elevated temperature. In a manner expedient in terms of application technology, the directly obtained multimetal oxide material M (preferably in finely divided form) is mixed with the wash liquid F and stirred under reflux for a few hours (as a rule from 1 to 10 hours). Typically used temperatures are from 50 to 100° C. After the end of the washing, the remaining solid is usually separated from the liquid phase by filtration and then washed, for example with water, to remove the wash medium. Finally, the washed solid is dried, expediently at elevated temperature.

According to the invention, it is noteworthy that the performance of directly obtained multimetal oxide materials M can be improved by the novel procedure, although, as shown by their X-ray diffraction pattern, they do not evidently contain the usually troublesome secondary phase which is generally readily soluble in the wash liquids F to be used according to the invention and is identified by its reflection at the peak position $2\Theta=50.0\pm0.3°$.

This may be due to the fact that directly obtained multimetal oxide materials M contain said secondary phase only in very tiny amounts as a coating on their surface, which is removed by the novel procedure, said amounts scarcely being detectable by X-ray diffraction.

All data based on an X-ray diffraction pattern in this document relate to an X-ray diffraction pattern produced using $CuK_\alpha$ radiation as X-rays (Siemens diffractometer Theta-Theta D-5000, tube voltage: 40 kV, tube current: 40 mA, aperture V20 (variable), collimator V20 (variable), secondary monochromator aperture (0.1 mm), detector aperture (0.6 mm), measuring interval (2θ):0.02°, measuring time per step: 2.4 s, detector: scintillation counter). In this document, the definition of the intensity of a reflection in the X-ray diffraction pattern is based on the definition stated in DE-A 19835247, DE-A 10122027 and in DE-A 10051419 and DE-A 10046672; the same applies to the definition of the full width at half height.

According to the invention, preferably $0.67 \leq R \leq 0.75$ and very particularly preferably R=0.69 to 0.75 or R=0.71 to 0.74 or R=0.72 for the multimetal oxide material M, both before and after washing according to the invention.

In addition to the reflections h, i and k, the X-ray diffraction pattern of multimetal oxide materials M, both before and after washing according to the invention, generally also contains further reflections whose peaks are at the following diffraction angles (2θ):

9.0±0.4° (l),
6.7±0.4° (o) and
7.9±0.4° (p).

It is furthermore advantageous if the X-ray diffraction pattern additionally contains a reflection whose peak is at the diffraction angle (2θ)=45.2±0.4° (q).

Frequently, the X-ray diffraction pattern of multimetal oxide materials M, both before and after washing according to the invention, also contains the reflections 29.2±0.4° (m) and 35.4±0.4° (n) (peak positions).

If the intensity 100 is assigned to the reflection h, it is advantageous, according to the invention, if the reflections i, l, m, n, o, p and q have, both before and after washing of the multimetal oxide material M according to the invention, the following intensities on the same intensity scale:

i: from 5 to 95, frequently from 5 to 80, in some cases from 10 to 60;
l: from 1 to 30;
m: from 1 to 40;
n: 1 to 40;
o: from 1 to 30;
p: from 1 to 30 and
q: from 5 to 60.

If the X-ray diffraction pattern of the multimetal oxide materials M obtainable according to the invention contains any of the abovementioned additional reflections, the FWHH thereof is as a rule ≦1°, both before and after washing according to the invention.

The specific surface area of the multimetal oxide materials M obtainable according to the invention is frequently from 1 to 40, frequently from 15 to 40 or 30, m²/g (determined by the BET method, nitrogen).

According to the invention, the stoichiometric coefficient a of the multimetal oxide materials M obtainable according to the invention is preferably from 0.05 to 0.6, particularly preferably from 0.1 to 0.6 or 0.5, independently of the preferred ranges for the other stoichiometric coefficients of the multimetal oxide materials M obtainable according to the invention.

Independently of the preferred ranges for the other stoichiometric coefficients of the multimetal oxide materials M obtainable according to the invention, the stoichiometric coefficient b is preferably from 0.01 to 1, particularly preferably from 0.01 or 0.1 to 0.5 or 0.4.

The stoichiometric coefficient c of the multimetal oxide materials M obtainable according to the invention is from 0.01 to 1, particularly preferably from 0.01 or 0.1 to 0.5 or 0.4, independently of the preferred ranges for the other stoichiometric coefficients of the multimetal oxide materials M obtainable according to the invention. A very particularly preferred range for the stoichiometric coefficient c, which, independently of the preferred ranges for the other stoichiometric coefficients of the multimetal oxide materials M obtainable according to the invention, can be combined with all other preferred ranges in this document, is from 0.05 to 0.2.

According to the invention, the stoichiometric coefficient d of the multimetal oxide materials M obtainable according to the invention is >0, and is preferably from 0.00005 or 0.0001 to 0.5, particularly preferably from 0.0005 to 0.3, frequently from 0.00075 to 0.2, often from 0.001 or 0.01 to 0.1, independently of the preferred ranges for the other stoichiometric coefficients of the multimetal oxide materials M obtainable according to the invention.

Particularly preferred multimetal oxide materials M obtainable according to the invention are those whose stoichiometric coefficients a, b, c and d are simultaneously in the following ranges:

a=from 0.05 to 0.6;
b=from 0.01 to 1 (or from 0.01 to 0.5);
c=from 0.01 to 1 (or from 0.01 to 0.5); and
d=from 0.0001 to 0.5 (or from 0.0005 to 0.3).

Very particularly advantageous multimetal oxide materials M obtainable according to the invention are those whose stoichiometric coefficients a, b, c and d are simultaneously in the following ranges:

a=from 0.1 to 0.6;
b=from 0.1 to 0.5;
c=from 0.1 to 0.5; and
d=from 0.00075 to 0.2 or from 0.001 to 0.01 or from 0.001 to 0.1.

$M^1$ is preferably Te.

All of the abovementioned applies in particular when, in the multimetal oxide materials M obtainable according to the invention, at least 50 mol % of the total amount of $M^2$ is Nb, very particularly preferably when at least 75 mol % or 100 mol % of the total amount of $M^2$ is Nb.

However, independently of the meaning of $M^2$, it also applies in particular when $M^3$ is at least one element from the group consisting of Ni, Co, Bi, Pd, Ag, Au, Pb and Ga or at least one element from the group consisting of Ni, Co, Pd und Bi.

However, all of the abovementioned also applies in particular when, in the multimetal oxide materials M obtainable according to the invention, at least 50 mol % of the total amount of $M^2$ or at least 75 mol % or 100 mol % is Nb and $M^3$ is at least one element from the group consisting of Ni, Co, Bi, Pd, Ag, Au, Pb and Ga.

However, all of the abovementioned also applies in particular when, in the multimetal oxide materials M obtainable according to the invention, at least 50 mol % or at least 75 mol % or 100 mol % of the total amount of $M^2$ is Nb and $M^3$ is at least one element from the group consisting of Ni, Co, Pd and Bi.

Very particularly preferably, all statements regarding the stoichiometric coefficients apply when, in the multimetal oxide materials M obtainable according to the invention, $M^1$ is Te, $M^2$ is Nb and $M^3$ is at least one element from the group consisting of Ni, Co and Pd.

Further stoichiometries suitable according to the invention for the multimetal oxide materials M obtainable according to the invention are those which are disclosed in the prior art cited at the outset.

Multimetal oxide materials M to be washed according to the invention may, under certain circumstances, be obtained, for example, by the preparation processes described in the documents DE-A 19835247, EP-A 529853, EP-A 603836, EP-A 608838, EP-A 895809, DE-A 19835247, EP-A 962253, EP-A 1080784, EP-A 1090684, EP-A 1123738, EP-A 1192987, EP-A 1192986, EP-A 1192982, EP-A 1192983 and EP-A 1192988. According to these processes, a very intimate, preferably finely divided, dry blend is produced from suitable sources of the elemental constituents of the multimetal oxide materials and said dry blend is thermally treated at from 350 to 700° C. or from 400 to 650° C. or from 400 to 600° C. The thermal treatment can in principle be effected under an oxidizing, reducing or inert atmosphere. A suitable oxidizing atmosphere is, for example, air, air enriched with molecular oxygen or air depleted in oxygen. The thermal treatment is, however, preferably carried out under an inert atmosphere, i.e. for example under molecular nitrogen and/or noble gas. Usually, the thermal treatment is effected at atmospheric pressure (1 atm). Of course, the thermal treatment can also be effected under reduced or superatmospheric pressure.

If the thermal treatment is effected under a gaseous atmosphere, this may be either stationary or flowing. It preferably flows. In general, the thermal treatment may take up to 24 hours or longer.

The thermal treatment is preferably first effected under an oxidizing (oxygen-containing) atmosphere (e.g. under air) at from 150 to 400° C. or from 250 to 350° C. (=preliminary decomposition step). The thermal treatment is then expediently continued under inert gas at from 350 to 700° C. or from 400 to 650° C. or from 450 to 600° C. Of course, the thermal treatment can also be effected by first pelleting the catalyst precursor material before its thermal treatment (if necessary, after pulverizing and with or without the addition of from 0.5 to 2% by weight of finely divided graphite), then subjecting it to thermal treatment and thereafter converting it into chips again.

The thorough mixing of the starting compounds can be effected in dry or in wet form.

If it is effected in dry form, the starting compounds are expediently used in the form of finely divided powders and, after mixing and, if required, compaction, are subjected to the calcination (thermal treatment).

However, the thorough mixing is preferably effected in wet form. Usually, the starting compounds are mixed with one another in the form of an aqueous solution (if required, in the presence of a complexing agent; cf. for example DE-A 10145958) and/or suspension. The aqueous material is then dried and is calcined after the drying. The aqueous material is expediently an aqueous solution or an aqueous suspension. The drying process is preferably effected immediately after the preparation of the aqueous mixture (particularly in the case of an aqueous solution, cf. for example JP-A 7-315842) and by spray drying (the exit temperatures are as a rule from 100 to 150° C.; the spray drying can be carried out by the cocurrent or countercurrent method), which results in a particularly intimate dry blend, especially when the aqueous material to be spray dried is an aqueous solution or suspension. However, it can also be dried by evaporating down under reduced pressure, by freeze drying or by conventional evaporating down.

Suitable sources for the elemental constituents when carrying out the preparation by the method described above are all those which are capable of forming oxides and/or hydroxides on heating (if required in air). Of course, oxides and/or hydroxides of the elemental constituents may themselves be concomitantly used or exclusively used as such starting compounds, i.e. in particular all starting compounds mentioned in the publications of the prior art considered are suitable.

Sources for the element Mo which are suitable according to the invention are, for example, molybdenum oxides, such as molybdenum trioxide, molybdates, such as ammonium heptamolybdate tetrahydrate, and molybdenum halides, such as molybdenum chloride.

Suitable starting compounds to be concomitantly used according to the invention for the element V are, for example, vanadium oxysulfate hydrate, vanadyl acetylacetonate, vanadates, such as ammonium metavanadate, vanadium oxides, such as vanadium pentoxide ($V_2O_5$), vanadium halides, such as vanadium tetrachloride ($VCl_4$) and vanadium oxyhalides, such as $VOCl_3$. Other vanadium starting compounds which may be present are those which contain vanadium in the oxidation stage +4.

Sources of the element tellurium which are suitable according to the invention are tellurium oxides, such as tellurium dioxide, metallic tellurium, tellurium halides, such as $TeCl_2$, and also telluric acids, such as orthotelluric acid $H_6TeO_6$.

Advantageous antimony starting compounds are antimony halides, such as $SbCl_3$, antimony oxides, such as antimony trioxide ($Sb_2O_3$), antimonic acids, such as $HSb(OH)_6$, and also antimony oxide salts, such as antimony oxide sulfate $(SbO)_2SO_4$.

Niobium sources suitable according to the invention are, for example, niobium oxides, such as niobium pentoxide ($Nb_2O_5$), niobium oxyhalides, such as $NbOCl_3$, niobium halides, such as $NbCl_5$, and also complex compounds of niobium and organic carboxylic acids and/or dicarboxylic acids, e.g. oxalates and alcoholates. Of course, the niobium-containing solutions used in EP-A 895809 are also suitable as a niobium source.

Regarding all other possible elements (in particular Pb, Ni, Cu, Co, Bi and Pd), suitable starting compounds are in particular their halides, nitrates, formates, oxalates, acetates, carbonates and/or hydroxides. Suitable starting compounds are often also their oxo compounds, e.g. tungstates, or the acids derived from these. Ammonium salts are also frequently used as starting compounds.

Other suitable starting compounds are polyanions of the Anderson type, as described, for example, in Polyhedron Vol. 6, No. 2, pages 213–218, 1987. A further suitable literature source for polyanions of the Anderson type is Kinetics and Catalysis, Vol. 40, No. 3, 1999, pages 401 to 404.

Other polyanions suitable as starting compounds are, for example, those of the Dawson and Keggin type. Preferably used starting compounds are those which are converted into their oxides at elevated temperatures, either in the presence or in the absence of oxygen, possibly with liberation of gaseous compounds.

The multimetal oxide materials M directly obtainable as described can then be converted into multimetal oxide materials M obtainable according to the invention by inventive washing in the manner described.

Very frequently, the preparation of multimetal oxide materials M to be washed according to the invention is successful when their preparation is carried out by a hydrothermal method, as described, for example, in DE-A 10029338 and JP-A 2000-143244, where a mixture of sources of the elemental constituents of the multimetal oxide material M is subjected to a hydrothermal treatment. The newly forming solid is separated off and, as a intimate drying blend, is converted in the manner described by thermal treatment into a multimetal oxide material M. The hydrothermal procedure is familiar to a person skilled in the art (cf. column 2, bottom, of DE-A 10029338). In particular, this is understood here as meaning the thermal treatment of a, preferably intimate, mixture of sources of the elemental constituents of the desired multimetal oxide material M in a vessel under superatmospheric pressure (autoclave) in the presence of steam at superatmospheric pressure, usually at temperatures in the range from >100° C. to 600° C. The pressure range is typically up to 500 atm, preferably up to 250 atm. Of course, temperatures above 600° C. and steam pressures above 500 atm can also be used, but it is not very expedient in terms of application technology. Typically advantageously, the hydrothermal treatment is carried out under conditions under which steam and liquid water coexist.

This is possible in the temperature range from >100° C. to 374.15° C. (critical temperature of water) with the use of the corresponding pressures.

The amounts of water are expediently such that the liquid phase is capable of taking up the total amount of the starting compounds in suspension and/or solution. However, a procedure is also possible in which the intimate mixture of the starting compounds completely absorbs the amount of liquid water present in equilibrium with the steam.

Advantageously, the hydrothermal treatment is effected at from >100 to 300° C., preferably from 150 to 250° C. (e.g. from 160 to 200° C.). Based on the sum of water and sources of the elemental constituents of the desired multimetal oxide material M, the amount by weight of the latter in the autoclave is as a rule at least 1% by weight. Usually, the abovementioned amount by weight is not above 90% by weight.

Amounts by weight of from 30 to 60 or from 5 to 30% by weight, frequently from 5 to 15% by weight, are typical.

During the hydrothermal treatment, stirring may or may not be carried out. The hydrothermal treatment itself takes as a rule a period of from a few hours to a few days. A period of 48 hours is typical.

It is expedient in terms of application technology if the autoclave to be used for the hydrothermal treatment is coated on the inside with Teflon. Before the hydrothermal treatment, the autoclave, if required including the aqueous mixture contained, can be evacuated. Before the temperature is increased it may be filled with inert gas ($N_2$, noble gas). Both measures can also be omitted. Of course, the aqueous mixture can additionally be flushed with inert gas before hydrothermal treatment to create inert conditions. In a manner expedient in terms of application technology, the abovementioned inert gases can also be used for establishing superatmospheric pressure in the autoclave even before the hydrothermal treatment.

The thermal treatment of the solid (intimate mixture) newly formed and separated off after the end of the hydrothermal treatment (after the end of the hydrothermal treatment, the autoclave can either be quenched to room temperature or brought slowly, i.e. over a relatively long period (e.g. by leaving it to stand) to room temperature), which thermal treatment is required for producing the multimetal oxide material M to be washed according to the invention, is expediently carried out (as in the case of the conventional preparation described above) at from 350 to 700° C., frequently from 400 to 650° C. or from 400 to 600° C. It can be effected under an oxidizing, reducing or inert atmosphere. A suitable oxidizing atmosphere is, for example, air, air enriched with molecular oxygen or air depleted in oxygen. The thermal treatment is preferably carried out under an inert atmosphere, for example under molecular nitrogen and/or noble gas. Of course, the thermal treatment can also be carried out under reduced pressure.

The preparation of multimetal oxide materials M to be treated according to the invention can, however, also be effected by first producing a multimetal oxide material M, which differs from a multimetal oxide material M only in that d is 0.

Such a preferably finely divided multimetal oxide material I' can then be impregnated with solutions (e.g. aqueous solutions) of elements $M^3$ (e.g. by spraying), then dried (preferably at $\leq 100°$ C.) and then calcined (preferably in an inert gas stream) as described above (here, preliminary decomposition in air is often dispensed with). The use of aqueous nitrate and/or halide solutions of elements $M^3$ and/or the use of aqueous solutions in which the elements $M^3$ are present as a complex with organic compounds (e.g. acetates or acetylacetonates) is particularly advantageous for this preparation variant.

The multimetal oxides M obtainable by washing according to the invention can be used as such [e.g. as a powder or after pelleting of the powder (frequently with addition of from 0.5 to 2% by weight of finely divided graphite) and subsequent comminution to give chips] or can be shaped into moldings as catalysts for heterogeneously catalyzed gas-phase partial oxidations and/or ammoxidations of saturated and/or unsaturated hydrocarbons. The catalyst bed may be a fixed bed, a moving bed or a fluidized bed.

The shaping to give moldings can be effected, for example, by application to a support, as described, for example, in DE-A 10118814 or PCT/EP/02/04073 or DE-A 10051419.

The supports to be used here for the multimetal oxide materials M obtainable according to the invention are preferably chemically inert, i.e. they substantially do not participate in the partial catalytic gas-phase oxidation or ammoxidation of the hydrocarbon (e.g. propane and/or propene to acrylic acid), which is catalyzed by the multimetal oxide materials M obtainable according to the invention.

According to the invention, particularly suitable materials for the supports are alumina, silica, silicates, such as clay, kaolin, steatite (preferably with a low water-soluble alkali content), pumice, aluminum silicate and magnesium silicate, silicon carbide, zirconium dioxide and thorium dioxide. Supports containing a minimal or tiny amount of alkali are used.

The surface of the support may be either smooth or rough. Advantageously, the surface of the support is rough since high surface roughness generally results in greater adhesive strength of the applied coat of active material.

Frequently, the surface roughness $R_z$ of the support is from 5 to 200 µm, often from 20 to 100 µm (determined according to DIN 4768, Sheet 1, using a Hommel Tester for DIN-ISO surface variables, from Hommelwerke, DE).

Furthermore, the support material may be porous or nonporous. Expediently, the support material is nonporous (total volume of pores, based on the volume of the support, <1% by volume).

The thickness of the active oxide material coat present on the novel coated catalysts is usually from 10 to 1 000 µm. However, it may also be from 50 to 700 µm, from 100 to 600 µm or from 150 to 400 µm. Possible coat thicknesses are also from 10 to 500 µm, from 100 to 500 µm or from 150 to 300 µm.

In principle, any geometries of the supports are suitable. Their longest dimension is as a rule from 1 to 10 mm. However, spheres or cylinders, in particular hollow cylinders, are preferably used as supports. Advantageous diameters for spherical supports are from 1.5 to 4 mm. If cylinders are used as supports, their length is preferably from 2 to 10 mm and their external diameter preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, a support ring geometry of 7 mm×3 mm×400 or of 5 mm×3 mm×2 mm (external diameter×length×internal diameter) is also possible.

The preparation of coated catalysts can be effected in the simplest manner by preforming oxide materials M obtainable according to the invention, converting them into finely divided form and finally applying them to the surface of the support with the aid of a liquid binder. For this purpose, the surface of the support is, in the simplest procedure, moistened with the liquid binder and a coat of the active material is bonded to the moistened surface by bringing it into contact with finely divided active oxide material M. Finally, the coated support is dried, of course, the procedure can be repeated periodically to obtain a greater coat thickness. In this case, the coated parent body becomes the new support, etc.

The fineness of the catalytically active oxide material M obtainable according to the invention which is to be applied to the surface of the support is of course adapted to the desired coat thickness. For the coat thickness range of from 100 to 500 µm, for example, those active material powders in which at least 50% of the total number of powder particles pass through a sieve of mesh size from 1 to 20 µm and whose numerical fraction of particles having a longest dimension above 50 µm is less than 10% are suitable. As a rule, the distribution of the longest dimensions of the powder particles corresponds to a Gaussian distribution as a result of the preparation. Frequently, the particle size distribution is as follows:

| D (µm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

Here:
D = diameter of the particle,
x = the percentage of particles whose diameter is $\geq$ D;
and
y = the percentage of particles whose diameter is < D.

For carrying out the coating method described on an industrial scale, it is advisable, for example, to use the basic method disclosed in DE-A 2909671 and that disclosed in DE-A 10051419, i.e. the supports to be coated are initially taken in a preferably inclined (the angle of inclination is as a rule $\geq 0°$ and $\leq 90°$, in general $\geq 30°$ and $\leq 90°$; the angle of inclination is the angle between the central axis of the rotating container and the horizontal) rotating container (e.g. rotating pan or coating drum). The rotating container conveys the, for example, spherical or cylindrical supports through two metering apparatuses arranged at a certain distance in succession. The first of the two metering apparatuses expediently corresponds to a nozzle (e.g. an atomizer nozzle operated with compressed air), through which the supports rolling in the rotating pan are sprayed with the liquid binder and moistened in a controlled manner. The second metering apparatus is present outside the atomization cone of the liquid binder sprayed in and serves for feeding in the finely divided oxidic active material M (e.g. via a vibrating chute or a powder screw). The spherical supports moistened in a controlled manner absorb the active material powder fed in, which is compacted by the rolling movement on the outer surface of the, for example, cylindrical or spherical support to form a cohesive coat.

If required, the support provided with a base coat in this manner passes again through the spray nozzle in the course of the subsequent revolution and is moistened in a controlled manner thereby, in order to be able to accept a further coat of finely divided oxidic active material in the course of the further movement (intermediate drying is as a rule not required). Finely divided oxidic active material M and liquid binder are as a rule fed in continuously and simultaneously.

The removal of the liquid binder can be effected after the end of the coating, for example by the action of hot gas, such as $N_2$ or air. Remarkably, the coating method described results in completely satisfactory adhesion both of the successive coats to one another and of the base coat to the surface of the support.

What is important for the coating method described above is that the moistening of the support surface to be coated is carried out in a controlled manner. In short, this means that the support surface is expediently moistened in such a way that, although adsorbed liquid binder is present on it, no liquid phase as such is visible on the support surface. If the support surface is too moist, the finely divided catalytically active oxide material agglomerates to form separate agglomerates instead of being applied to the surface. Detailed information in this context can be found in DE-A 2909671 and in DE-A 10051419.

The abovementioned final removal of the liquid binder used can be carried out in a controlled manner, for example by evaporation and/or sublimation. In the simplest case, this can be effected by the action of hot gases at an appropriate temperature (frequently from 50 to 300° C., often 150° C.). However, preliminary drying only can be effected by the action of hot gases. The final drying can then be carried out, for example, in a drying oven of any desired type (e.g. belt dryer) or in the reactor. The temperature applied should not be above the calcination temperature used for the preparation of the oxidic active material. Of course, the drying can also be carried out exclusively in a drying oven.

The following may be used as a binder for the coating process, regardless of the type and geometry of the support: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Advantageous binders are also solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. Advantageously, the organic compound is selected from the above list of possible organic binders. Preferably, the organic proportion of abovementioned aqueous binder solutions is from 10 to 50, particularly preferably from 20 to 30, % by weight. Other suitable organic components are monosaccharides and oligosaccharides, such as glucose, fructose, sucrose or lactose, and polyethylene oxides and polyacrylates.

Of course, the shaping of multimetal oxide materials M obtainable according to the invention can also be effected by extrusion and/or pelleting of finely divided multimetal oxide material M obtainable according to the invention.

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Annular unsupported catalysts suitable according to the invention can also have a length of from 3 to 6 mm, an external diameter of from 4 to 8 mm and a wall thickness of from 1 to 2 mm. However, unsupported catalyst rings measuring 7 mm×3 mm×4 mm or 5 mm×3 mm×2 mm (external diameter×length×internal diameter) are also possible.

Of course, suitable geometries of the multimetal oxide active materials M obtainable according to the invention to be used as catalysts are also all those of DE-A 10101695.

As stated above, the definition of the intensity of a reflection in the X-ray diffraction pattern in this document is based on the definition given in DE-A 19835247, and the definition given in DE-A 10051419 and DE-A 10046672.

This means that if $A^1$ is the peak of a reflection 1 and $B^1$ is the next pronounced minimum (minima having reflection shoulders are not taken into account), to the left of the peak $A^1$ in the line of the X-ray diffraction pattern when viewed along the intensity axis perpendicular to the $2\theta$ axis, and $B^2$ is, in a corresponding manner, the next pronounced minimum to the right of the peak $A^1$ and $C^1$ is the point at which a straight line drawn from the peak $A^1$ perpendicular to the $2\theta$ axis intersects a straight line connecting the points $B^1$ and $B^2$, then the intensity of the reflection 1 is the length of the straight segment $A^1C^1$ which extends from the peak $A^1$ to the point $C^1$. The expression minimum means a point at which the gradient of a tangent to the curve in a base region of the reflection 1 changes from a negative value to a positive value, or a point at which the gradient tends to zero, the coordinates of the $2\theta$ axis and of the intensity axis being used for determining the gradient.

In this document, the FWHH is, in a corresponding manner, the length of the straight segment between the two points of intersection $H^1$ and $H^2$ when the line parallel to the $2\theta$ axis is drawn in the middle of the straight segment $A^1C^1$, $H^1$, $H^2$ meaning the first point of intersection of this parallel line in each case with the line of the X-ray diffraction pattern, as defined above, to the left and right of $A^1$.

An exemplary procedure for determining FWHH and intensity is also shown in FIG. 6 in DE-A 10046672.

Of course, the multimetal oxide materials M obtainable according to the invention can also be employed as catalytically active materials in a form diluted with finely divided, e.g. colloidal, materials, such as silica, titanium dioxide, alumina, zirconium oxide or niobium oxide.

The dilution mass ratio may be up to 9 (diluent):1 (active material), i.e. possible dilution mass ratios are, for example, 6 (diluent):1 (active material) and 3 (diluent):1 (active material). The incorporation of the diluents can be effected before and/or after the calcination during the preparation of the multimetal oxide materials M to be washed according to the invention, as a rule even before the drying.

If the incorporation is effected before the drying or before the calcination, the diluent must be chosen so that it remains substantially unchanged in the fluid medium or during the calcination. This generally occurs, for example, in the case of oxides calcined at appropriately high temperatures.

The multimetal oxide materials M obtainable according to the invention are, as mentioned above, suitable as such or in dilute form as described above as active materials for heterogeneously catalyzed partial gas-phase oxidations (including oxydehydrogenations) and/or ammoxidations of saturated and/or unsaturated hydrocarbons.

Such saturated and/or unsaturated hydrocarbons are in particular ethane, ethylene, propane, propylene, n-butane, isobutane and butenes, such as 2-butene and isobutene. Desired products are in particular acrolein, acrylic acid, methacrolein, methacrylic acid, acrylonitrile and methacrylonitrile. However, they are also suitable for the heterogeneously catalyzed partial gas-phase oxidation and/or ammoxidation of compounds such as acrolein and methacrolein.

However, ethylene, propylene and acetic acid may also be desired products.

Complete oxidation of the hydrocarbon is understood in this document as meaning that the total amount of carbon contained in the hydrocarbon was converted into oxides of carbon ($CO$, $CO_2$).

All reactions of the hydrocarbons under the reactive influence of molecular oxygen which differ therefrom are subsumed in this document by the term partial oxidation. The additional reactive influence of ammonia is a feature of partial ammoxidation.

Multimetal oxide materials M obtainable according to the invention described in this document are preferably suitable as catalytically active materials for the conversion of propane to acrolein and/or acrylic acid, of propane to acrylic acid and/or acrylonitrile, of propylene to acrolein and/or acrylic acid, of propylene to acrylonitrile, of isobutane to methacrolein and/or methacrylic acid, of isobutane to methacrylic acid and/or methacrylonitrile, of ethane to ethylene, of ethane to acetic acid and of ethylene to acetic acid.

The procedure for such partial oxidations and/or ammoxidations (by the choice of the ammonia content in the reaction mixture, to be controlled in a manner known per se, the reaction can be designed substantially exclusively as a partial oxidation or exclusively as a partial ammoxidation, or as a superposition of the two reactions; cf. for example WO 98/22421) is known per se and can be carried out in a completely corresponding manner.

If the hydrocarbon used is crude propane or crude propylene, this preferably has the composition as described in DE-A 10246119 or DE-A 10118814 or PCT/EP/02/04073. The procedure is preferably also effected as described there.

A partial oxidation of propane to acrylic acid which is to be carried out using catalysts comprising multimetal oxide M obtainable according to the invention as active material can be carried out, for example, as described in EP-A 608838, WO 0029106, JP-A 10-36311, EP-A 1193240 and EP-A 1192987.

For example, air, air enriched with oxygen, air depleted in oxygen or pure oxygen can be used as a source of the required molecular oxygen.

Such a process is also advantageous when the reaction gas starting mixture contains no noble gas, in particular no helium, as inert diluent gas. Otherwise, the reaction gas starting mixture can of course comprise inert diluent gases, e.g. $N_2$, $CO$ and $CO_2$, in addition to propane and molecular oxygen. Steam as a component of the reaction gas mixture is advantageous according to the invention.

This means that the reaction gas starting mixture with which the multimetal oxide active material M obtainable according to the invention is to be loaded at reaction temperatures of, for example, from 200 to 550° C. or from 230 to 480° C. or from 300 to 440° C. and pressures of from 1 to 10 or from 2 to 5 bar may have, for example, the following composition:

from 1 to 15, preferably from 1 to 7, % by volume of propane,
from 44 to 99% by volume of air and
from 0 to 55% by volume of steam.

Steam-containing reaction gas starting mixtures are preferred.

The following are suitable as other possible compositions of the reaction gas starting mixture:

from 70 to 95% by volume of propane,
from 5 to 30% by volume of molecular oxygen and
from 0 to 25% by volume of steam.

In such a process, a product gas mixture which does not consist exclusively of acrylic acid is of course obtained. Rather, the product gas mixture contains, in addition to unconverted propane, secondary components such as propene, acrolein, $CO_2$, $CO$, $H_2O$, acetic acid, propionic acid, etc., from which the acrylic acid has to be separated off.

This can be effected in the manner known from the heterogeneously catalyzed gas-phase oxidation of propene to acrylic acid.

This means that the acrylic acid present can be taken up from the product gas mixture by absorption with water or by absorption with a high-boiling inert hydrophobic organic solvent (for example, a mixture of diphenyl ether and diphyl, which, if required, may also contain additives such as dimethyl phthalate). The resulting mixture of absorbent and acrylic acid can then be worked up by rectification, extraction and/or crystallization in a manner known per se to give the pure acrylic acid.

Alternatively, the basic separation of the acrylic acid from the product gas mixture can also be effected by fractional condensation, as described, for example, in DE-A 19 924 532.

The resulting aqueous acrylic acid condensate can then be further purified, for example by fractional crystallization (e.g. suspension crystallization and/or layer crystallization).

The residual gas mixture remaining in the basic separation of the acrylic acid contains in particular unconverted propane, which is preferably recycled to the gas-phase oxidation. For this purpose, it can be partly or completely separated from the residual gas mixture, for example by fractional rectification under superatmospheric pressure, and then recycled to the gas-phase oxidation. However, it is more advantageous to bring the residual gas into contact, in an extraction apparatus, with a hydrophobic organic solvent (e.g. by passing the latter through) which is capable of absorbing propane.

By subsequent desorption and/or stripping with air, the absorbed propane can be liberated again and can be recycled to the novel process. In this way, economical total propane conversions can be achieved. As in other separation processes, propene formed as a secondary component is as a rule not separated or not completely separated from the propane and is circulated with the latter. This also applies in the case of other homologous saturated and olefinic hydrocarbons. In particular, it applies very generally for partial oxidations and/or ammoxidations of saturated hydrocarbons heterogeneously catalyzed with multimetal oxide materials M obtainable according to the invention.

It is advantageous that the multimetal oxide materials M obtainable according to the invention are also capable of heterogeneously catalyzing the partial oxidation and/or ammoxidation of the homologous olefinic hydrocarbon to the same desired product.

Thus, using the multimetal oxide materials M obtainable according to the invention as active materials, acrylic acid can be prepared by heterogeneously catalyzed partial gas-phase oxidation of propene with molecular oxygen, as described in DE-A 10118814 or PCT/EP/02/04073 or JP-A 7-53448.

This means that a single reaction zone A is sufficient for carrying out the novel process. Exclusively catalysts comprising multimetal oxide materials M obtainable according to the invention are present as catalytically active materials in this reaction zone.

This is unusual since the heterogeneously catalyzed gas-phase oxidation of propene to acrylic acid takes place very generally in two steps effected in succession in terms of time. In the first step, usually propene is substantially oxidized to acrolein and, in the second step, usually acrolein formed in the first step is oxidized to acrylic acid.

Conventional processes for the heterogeneously catalyzed gas-phase oxidation of propene to acrylic acid therefore usually use a special catalyst type tailored to the oxidation step for each of the two abovementioned oxidation steps.

This means that the conventional processes for the heterogeneously catalyzed gas-phase oxidation of propene to acrylic acid operate with two reaction zones, in contrast to the novel process.

In the process for the partial oxidation of propene catalyzed with multimetal oxide materials M obtainable according to the invention in the one reaction zone A, it is of course possible for only one or more than one catalyst comprising multimetal oxide materials M obtainable according to the invention to be present. Of course, the catalysts obtainable according to the invention can be diluted with inert material, as was recommended in this document, for example, also as support material.

In the process for the partial oxidation of propene catalyzed with multimetal oxide materials M obtainable according to the invention, it is possible for only one temperature or a temperature changing along the reaction zone A to prevail along the one reaction zone A, said temperature being produced by a heating medium for heating the reaction zone. This temperature change may then increase or decrease.

If such a process for the partial oxidation of propene is carried out as a fixed-bed oxidation, it is expediently carried out in a tube-bundle reactor whose catalyst tubes are loaded with the catalyst. Usually, a liquid, as a rule a salt bath, is passed as a heating medium around the catalyst tubes.

A plurality of temperature zones along the reaction zone A can then be realized in a simple manner if more than one salt bath is passed around the catalyst tubes segment by segment along the catalyst tubes.

When considered over the reactor, the reaction gas mixture in the catalyst tubes is fed either cocurrent with or countercurrent to the salt bath. The salt bath itself can execute purely parallel flow relative to the catalyst tubes. However, a transverse flow can of course also be superposed on said parallel flow. Overall, the salt bath can also execute, around the catalyst tubes, a meandering flow which is cocurrent with or countercurrent to the reaction gas mixture only when considered over the reactor.

In the novel process for the partial oxidation of propene, the reaction temperature may be from 200 to 500° C. along the total reaction zone A. Usually, it is from 250 to 450° C. Preferably, the reaction temperature is from 330 to 420° C., particularly preferably from 350 to 400° C.

In the process for the partial oxidation of propene catalyzed with multimetal oxide materials M obtainable according to the invention, the operating pressure may be 1 bar, less than 1 bar or more than 1 bar. Operating pressures typical according to the invention are from 1.5 to 10, frequently from 1.5 to 5, bar.

The propene to be used for this process for the partial oxidation of propene does not have to meet any particularly high requirements with respect to its purity.

As stated above and as is true very generally for all one- or two-stage processes for the heterogeneously catalyzed gas-phase oxidation of propene to acrolein and/or acrylic acid, for example propene (also referred to as crude propene) having the following two specifications can be used entirely without problems as propene for such a process:

Polymer-Grade Propylene:

| | |
|---|---|
| ≧99.6% by weight | Propene, |
| ≦0.4% by weight | Propane, |
| ≦300 ppm by weight | Ethane and/or methane, |
| ≦5 ppm by weight | $C_4$-hydrocarbons, |
| ≦1 ppm by weight | Acetylene, |
| ≦7 ppm by weight | Ethylene, |
| ≦5 ppm by weight | Water, |
| ≦2 ppm by weight | $O_2$, |
| ≦2 ppm by weight | Sulfur-containing compounds (calculated as sulfur), |
| ≦1 ppm by weight | Chlorine-containing compounds (calculated as chlorine), |
| ≦5 ppm by weight | $CO_2$, |
| ≦5 ppm by weight | CO, |
| ≦10 ppm by weight | Cyclopropane, |
| ≦5 ppm by weight | Propadiene and/or propyne, |
| ≦10 ppm by weight | $C_{\geq 5}$-hydrocarbons and |
| ≦10 ppm by weight | Carbonyl-containing compounds (calculated as $Ni(CO)_4$). | b) Chemical-Grade Propylene:

| | |
|---|---|
| ≧94% by weight | Propene, |
| ≦6% by weight | Popane, |
| ≦0.2% by weight | Methane and/or ethane, |
| ≦5 ppm by weight | Ethylene, |
| ≦1 ppm by weight | Acetylene, |
| ≦20 ppm by weight | Propadiene and/or propyne, |
| ≦100 ppm by weight | Cyclopropane, |
| ≦50 ppm by weight | Butene, |

| | -continued |
|---|---|
| ≦50 ppm by weight | Butadiene, |
| ≦200 ppm by weight | $C_4$-hydrocarbons, |
| ≦10 ppm by weight | $C_{\geq 5}$-hydrocarbons, |
| ≦2 ppm by weight | Sulfur-containing compounds (calculated as sulfur), |
| ≦0.1 ppm by weight | Sulfides (calculated as $H_2S$), |
| ≦1 ppm by weight | Chlorine-containing compounds (calculated as chlorine), |
| ≦0.1 ppm by weight | Chlorides (calculated as $Cl^{\ominus}$) and |
| ≦30 ppm by weight | Water. |

Of course, all abovementioned possible impurities in the propene can however each also be present in from two to ten times the stated individual amount in the crude propene without the usability of the crude propene for the described process or for the known processes for the one- or two-stage heterogeneously catalyzed gas-phase oxidation of propene to acrolein and/or acrylic acid very generally being adversely affected.

This applies in particular when the saturated hydrocarbons, the steam, the oxides of carbon and the molecular oxygen are compounds which participate either as inert diluent gases or as reactants in large amounts in the reaction in the abovementioned process. Usually, the crude protein as such is mixed with recycle gas, air and/or molecular oxygen and/or dilute air and/or inert gas before being used for the described process and all other processes of the heterogeneously catalyzed gas-phase oxidation of propene to acrolein and/or acrylic acid.

However, another suitable propene source for the described process is propene which contains, for example, up to 40% by weight of propane. This propene may additionally be accompanied by other impurities which substantially do not interfere with the process catalyzed with catalysts comprising multimetal oxide materials M obtainable according to the invention.

Both pure oxygen and air or air enriched with or depleted in oxygen can be used as an oxygen source for this process for the partial oxidation of propene.

In addition to molecular oxygen and propene, the reaction gas starting mixture to be used for such a process usually also contains at least one diluent gas. Suitable diluent gases are nitrogen, oxides of carbon, noble gases and lower hydrocarbons, such as methane, ethane and propane (higher hydrocarbons, e.g. $C_4$-hydrocarbons, should be avoided). Frequently, steam is also used as a diluent gas. Often, mixtures of abovementioned gases form the diluent gas for the novel process for the partial oxidation of propene.

The described heterogeneously catalyzed partial oxidation of propene is advantageously effected in the presence of propane.

Typically, the reaction gas starting mixture for a process for the partial oxidation of propene has the following composition (molar ratios):

Propene:oxygen:$H_2O$:other diluent gases=1:(0.1–10):(0–70):(0–20).

The abovementioned ratio is preferably 1:(1–5):(1–40):(0–10).

If propane is used as diluent gas, it can, as described, advantageously likewise be partly oxidized to acrylic acid in the described process.

The reaction gas starting mixture preferably contains molecular oxygen, CO, $CO_2$, steam and propane as diluent gas.

The molar propane:propene ratio in the described process may assume the following values: from 0 to 15, frequently from 0 to 10, often from 0 to 5, expediently from 0.01 to 3. The loading of the catalyst bed with propene in the described process for the partial oxidation of propene is, for example, from 40 to 250 l(S.T.P.)/l·h. The loading with reaction gas starting mixture is frequently from 500 to 15 000, often from 600 to 10 000, frequently from 700 to 5 000, l(S.T.P.)/l·h.

In the novel process for the partial oxidation of propene to acrylic acid, the product gas mixture obtained does not of course consist exclusively of acrylic acid. Rather, the product gas mixture contains, in addition to unconverted propene, secondary components such as propane, acrolein, $CO_2$, CO, $H_2O$, acetic acid, propionic acid, etc., from which the acrylic acid has to be separated off.

This can be effected in a manner known generally from the heterogeneously catalyzed two-stage gas-phase oxidation (carried out in two reaction zones) of propene to acrylic acid.

This means that the acrylic acid present can be taken up from the product gas mixture by absorption with water or by absorption with a high-boiling inert hydrophobic organic solvent (for example, a mixture of diphenyl ether and diphyl, which, if required, may also contain additives such as dimethyl phthalate). The resulting mixture of absorbent and acrylic acid can then be worked up by rectification, extraction and/or crystallization in a manner known per se to give the pure acrylic acid. Alternatively, the basic separation of the acrylic acid from the product gas mixture can also be effected by fractional condensation, as described, for example, in DE-A 19 924 532.

The resulting aqueous acrylic acid condensate can then be further purified, for example, by fractional crystallization (e.g. suspension crystallization and/or layer crystallization).

The residual gas mixture remaining in the basic separation of acrylic acid contains in particular unconverted propene (and may contain propane). This can be separated from the residual gas mixture, for example by fractional rectification under superatmospheric pressure, and then recycled to the described gas-phase partial oxidation. However, it is more advantageous to bring the residual gas into contact, in an extraction apparatus, with a hydrophobic organic solvent (e.g. by passing the latter through) which is capable of preferentially absorbing the propene (and any propane).

By subsequent desorption and/or stripping with air, the absorbed propene (and any propane) can be liberated again and recycled to the novel process. In this way, economical overall propene conversions can be achieved. If propene is subjected to partial oxidation in the presence of propane, propene and propane are preferably separated off and recycled together.

In a completely corresponding manner, the multimetal oxides M obtainable according to the invention can be used as catalysts for the partial oxidation of isobutane and/or isobutene to methacrylic acid.

Their use for the ammoxidation of propane and/or propene can be effected, for example, as described in EP-A 529853, DE-A 2351151, JP-A 6-166668 and JP-A 7-232071.

Their use for the ammoxidation of n-butane and/or n-butene can be effected as described in JP-A 6-211767.

Their use for the oxydehydrogenation of ethane to ethylene or the further reaction to acetic acid can be effected as described in U.S. Pat. No. 4,250,346 or as described in EP-B 261264.

The multimetal oxide materials M obtainable according to the invention can, however, also be integrated in other multimetal oxide materials (for example, their finely divided materials can be mixed, if required compressed and calcined or can be mixed as sludges (preferably aqueous), dried and calcined (for example as described in EP-A 529853 for multimetal oxide materials M to be washed according to the invention with d=0)). Preferably, once again calcination is effected under inert gas.

The resulting multimetal oxide materials (referred to below as overall materials) preferably contain $\geq 50$, particularly preferably $\geq 75$, very particularly preferably $\geq 90$ or $\geq 95$, % by weight of multimetal oxide materials M obtainable according to the invention and are likewise suitable for the partial oxidations and/or ammoxidations discussed in this document.

The overall materials also preferably have no reflection peak position at $2\Theta=50.0\pm3.0°$.

If the overall material has a reflection peak position at $2\theta=50.0\pm3.0°$, it is advantageous if the amount by weight of the multimetal oxide materials M obtainable according to the invention is $\geq 80$ or $\geq 90$ or $\geq 95\%$ by weight.

The geometric shaping is expediently effected in the case of the overall materials as described for the multimetal oxide materials M obtainable according to the invention.

The advantageousness of the multimetal oxide materials M obtainable according to the invention is based on their excellent selectivity with respect to the desired product, in particular with regard to both the partial oxidations mentioned in the document and partial ammoxidations.

For the purpose of the heterogeneously catalyzed partial gas-phase oxidation of propane to acrylic acid, the multimetal oxide materials M obtainable according to the invention and multimetal oxide materials or catalysts containing them are preferably put into operation as described in DE-A 10122027.

EXAMPLES

A) Preparation of Coated Catalysts Comprising Multimetal Oxide Materials

Comparative Example (Preparation of a Multimetal Oxide Catalyst Comprising an Active Substance $Mo_{1.0}V_{0.28}Te_{0.11}Nb_{0.16}O_x$, Which is a Multimetal Oxide Material M Obtained According to the Invention)

100 g of ammonium heptamolybdate (81.5% by weight of $MoO_3$, from Starck/Goslar) were dissolved together with 9.4 g of telluric acid (99% by weight of $H_6TeO_6$, from Aldrich) at 50° C. in the stated sequence in 423 ml of water, a solution 1 being obtained.

In a second container likewise at 50° C., 35.83 g of ammonium niobium oxalate (21.0% by weight of Nb, from Starck/Goslar) were dissolved together with 9.4 g of the abovementioned telluric acid in the stated sequence in 423 ml of water, a solution 2 being obtained. A third solution was prepared by dissolving 41.1 g of vanadium(IV) oxysulfate (20.1% by weight of V, from Aldrich) in 500 ml of water at 50° C., a solution 3 being obtained. The solution 2 was then stirred into the solution 1 in the course of 0.5 minute with stirring while maintaining the 50° C. Solution 3 was stirred into the resulting mixture, likewise while maintaining the 50° C., in the course of 1.5 minutes. The resulting aqueous suspension was then introduced into a steel autoclave having an internal volume of 2 300 ml and heated to 175° C. without stirring in the closed autoclave (in the course of 60 minutes). After a residence time of 48 hours at 175° C. without stirring in the autoclave, the autoclave was cooled to 25° C. by leaving it to stand and was opened and the solid contained in the liquid phase was filtered off from the solution, washed with 50 ml of water at 25° C. and dried at 40° C. for 12 hours.

Figure 2:
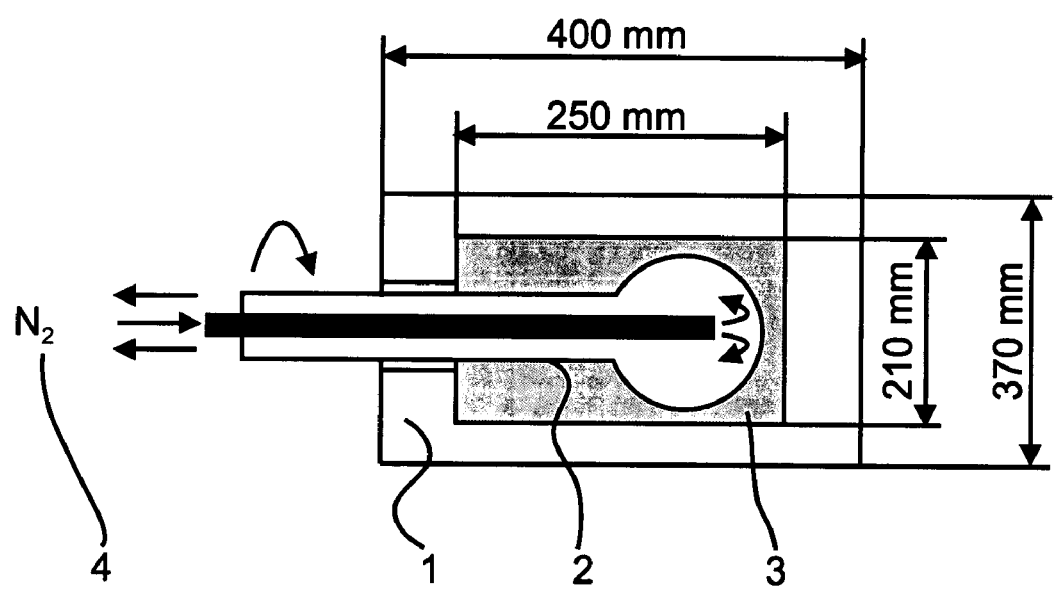
FIG. 2 shows a rotating bulb furnace (quartz glass bulb having an internal volume of liter; 1=furnace housing, 2=rotating bulb, 3=heated chamber, 4=nitrogen/air stream).

100 g of the dried solid, whose X-ray diffraction pattern is shown in FIG. 1, were heated in a rotating bulb furnace according to FIG. 2 (quartz glass bulb having an internal volume of 1 liter; 1=furnace housing, 2=rotating bulb, 3=heated space, 4=nitrogen/air stream) under an air stream of 50 llS.T.P.)/h in the course of 25 minutes, initially linearly from 25 to 250° C., and this temperature and the airstream were then maintained for 1 hour. Immediately thereafter, the air stream was replaced by a nitrogen stream of 50 l(S.T.P.)/h and heating was effected linearly from 250° C. to 600° C. in the course of 35 minutes. This temperature and the nitrogen stream were then maintained for 2 hours. Finally the entire rotating bulb furnace was cooled to 25° C. while maintaining the nitrogen stream.

Figure 3:
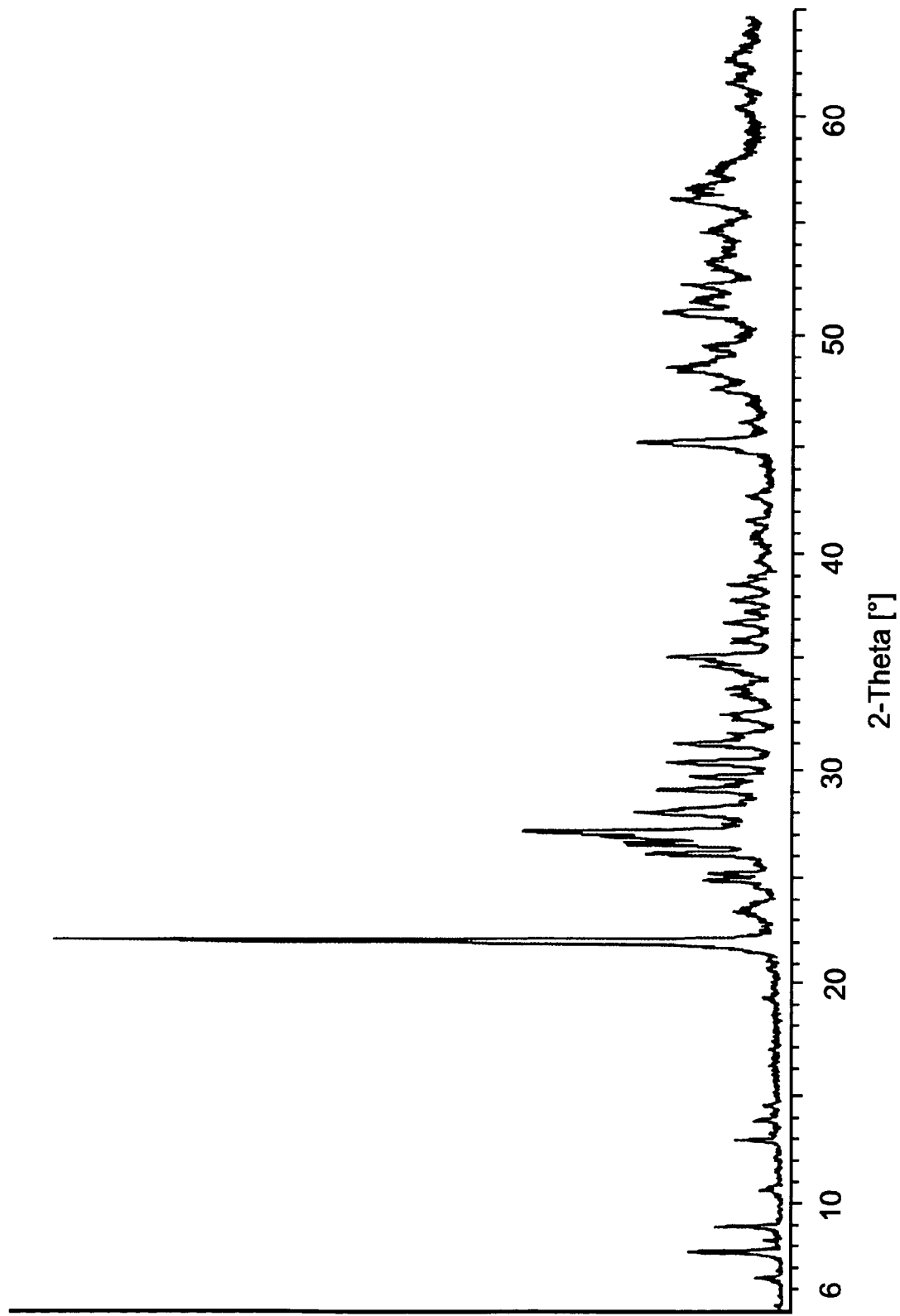
FIG. 3 shows the associated X-ray diffraction pattern of the Comparative Example after heating in a rotating bulb furnace.

A black powder having the composition $Mo_{1.0}V_{0.28}Te_{0.11}Nb_{0.16}O_x$ was obtained. This associated X-ray diffraction pattern is shown in FIG. 3.

The active material powder was then milled in a Retsch mill (centrifugal mill, type ZM 100, from Retsch, DE) (particle size $\leq 0.12$ mm).

38 g of the powder present after milling was applied to 150 g of spherical supports having a diameter of from 2.2 to 3.2 mm ($R_z=45$ µm, support material=steatite from Ceramtec, DE, total pore volume of the support $\leq 1\%$ by volume, based on the total support volume). For this purpose, the support was initially taken in a coating drum having an internal volume of 2 l (angle of inclination of the central axis of the drum relative to the horizontal=30°). The drum was rotated at 25 revolutions per minute. About 25 ml of a mixture of glycerol and water (glycerol:water weight ratio=1:3) were sprayed onto the support for 60 minutes via an atomizer nozzle operated with 300 l(S.T.P.)/h of compressed air. The nozzle was installed in such a way that the spray cone wetted the supports conveyed in the drum by lifting plates to the uppermost point of the inclined drum, in the upper half of the rolling zone. The finely divided active material powder was introduced into the drum via a powder screw, the point of addition of the powder being within the rolling zone or below the spray cone. By a periodic repetition of the wetting and powder metering, the support provided with a base coat itself became the support in the subsequent period.

After completion of coating, the coated support was dried under air for 16 hours at 150° C. in a muffle furnace. A coated catalyst CE1 comprising 20% by weight of active material resulted.

Example (Preparation of a Multimetal Oxide Catalyst Comprising an Active Material $Mo_{1.0}V_{0.22}Te_{0.09}Nb_{0.17}O_x$, Which is a Multimetal Oxide Material M Obtained According to the Invention)

Figure 4:
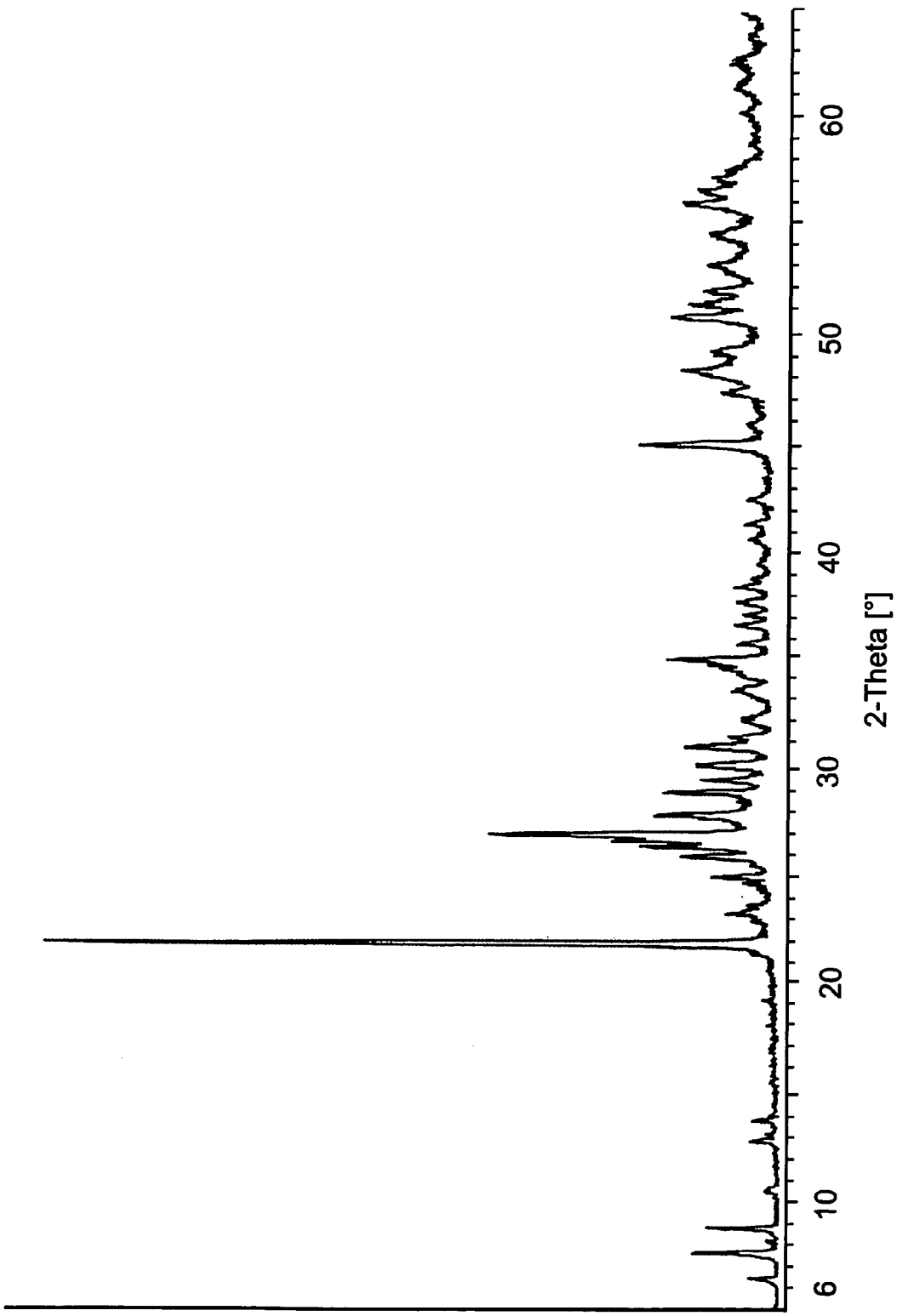
FIG. 4 shows the associated X-ray diffraction pattern of the Example.

100 g of a black active material powder $Mo_{1.0}V_{0.28}Te_{0.11}Nb_{0.16}O_x$ according to the comparative example were stirred under reflux in 1000 ml of a 10% strength by weight aqueous HNO$_3$ solution for 7 hours at 70° C. The remaining solid was filtered off from the resulting suspension and washed nitrate-free with water. The remaining filter cake was dried for 12 hours under air at 110° C. in a muffle furnace. The resulting dry active material had the composition Mo$_{1.0}$V$_{0.22}$Te$_{0.9}$Nb$_{0.17}$O$_x$. The associated X-ray diffraction pattern is shown in FIG. 4.

It was milled in the same manner as in the comparative example and applied to the same support, so that a coated catalyst B1 likewise comprising 20% of active material resulted.

B) Testing of the Coated Catalysts Prepared in A) and Comprising Multimetal Oxide Materials A tubular reactor produced from steel (internal diameter: 8.5 mm, length: 140 mm, wall thickness: 2.5 cm) was loaded in each case with 35.0 g of the respective coated catalyst from A) (catalyst bed length in all cases about 53 cm). A 30 cm preliminary bed of steatite beads (diameter: from 2.2 to 3.2 mm, manufacturer: Ceramtec) was installed before the catalyst bed, and a subsequent bed of the same steatite beads after the catalyst bed, over the remaining length of the tubular reactor.

The external temperature of the loaded reaction tube was brought to 350° C. over the total length from the outside by means of electrically heated heating mats.

The reaction tube was then fed with a reaction gas starting mixture having the molar propane:air:H$_2$O composition of 1:15:14 (the entrance side was on the side of the subsequent bed). The residence time (based on the catalyst bed volume) was brought to 2.4 seconds. The entrance pressure was 2 bar absolute.

The reaction tube load was initially operated in each case at the abovementioned external temperature of the loaded reaction tube over a period of 24 hours before this external temperature was increased to the respective reaction temperature shown in the table below.

The table below shows the resulting propane conversion (C$_{PAN}$) based on a single pass through the reaction tube at this external temperature T (° C.), and the resulting selectivity of the acrylic acid formation (S$_{ACA}$ (mol %) and the selectivity of the propene byproduct formation (S$_{PEN}$ (mol %)), depending on the coated catalyst used. In addition, the table shows the intensity ratio R of the active material present on the coated catalyst.

| Example | R | T (° C.) | C$_{PAN}$ (mol %) | S$_{ACA}$ (mol %) | S$_{PEN}$ |
|---|---|---|---|---|---|
| CE 1 | 0.66 | 390 | 15.42 | 49.23 | 19.55 |
| E1 | 0.75 | 390 | 30.73 | 67.63 | 9.21 |

We claim:

1. A process for preparing a multimetal oxide material M of the stoichiometry I:

wherein

M$^1$ is at least one of the elements selected from the group consisting of Te and Sb;

M$^2$ is at least one of the elements selected from the group consisting of Nb, Ti, W, Ta and Ce;

M$^3$ is at least one of the elements selected from the group consisting of Pb, Ni, Co, Bi, Pd, Ag, Pt, Cu, Au, Ga, Zn, Sn, In, Re, Ir, Sm, Sc, Y, Pr, Nd and Tb;

a is from 0.01 to 1, b is from >0 to 1, c is from >0 to 1, d is from >0 to 0.5 and n is a number which is determined by the valency and frequency of the elements other than oxygen in (I), whose X-ray diffraction pattern has reflections h, i and k, whose peaks are at the diffraction angles (2θ) 22.2±0.5° (h), 27.3±0.5°(i) and 28.2±0.5°(k), the reflection h being the one with the strongest intensity within the X-ray diffraction pattern and having a full width at half height (FWHH) of not more than 0.5°, the intensity P$_i$ of the reflection i and the intensity P$_k$ of the reflection k satisfying the relationship 0.65≦R≦0.85, wherein R is the intensity ratio defined by the formula $$R=P_i/(P_i+P_k)$$

and the FWHH of the reflection i and that of the reflection k being each±1°, but has no reflection having the peak position 2θ=50.0±0.3°;

the process comprising washing the multimetal oxide material M with a liquid selected from the group consisting of organic acids, inorganic acids, solutions of organic acids, solutions of inorganic acids and mixtures thereof, wherein the multimetal oxide material M is prepared with the proviso that, in the course of the preparation of the multimetal oxide material M, no precursor multimetal oxide material of the multimetal oxide material M is washed with a liquid selected from the group consisting of organic acids, inorganic acids, solutions of organic acids, solutions of inorganic acids, solutions of inorganic acids and mixtures thereof.

2. The process as claimed in claim 1, wherein the liquid with which washing is effected is an aqueous nitric acid solution.

3. The process as claimed in claim 1, wherein the X-ray diffraction pattern of the multimetal oxide material M to be washed contains, in addition to the reflections h, i and k, also further reflections whose peaks are at the following diffraction angles 2θ:

9.0±0.4°(l)

6.7±0.4°(o) and 7.9±0.4°(p).

4. The process as claimed in claim 3, wherein the X-ray diffraction pattern of the multimetal oxide material M to be washed contains, in addition to the reflections h, i, k, l, o and p, also further reflections whose peaks are at the following diffraction angles 2θ:

45.2±0.4°(q), 29.2±0.4°(m) and 35.4≅0.4°(n).

5. The process as claimed in claim 4, wherein the X-ray diffraction pattern of the multimetal oxide material M to be washed has the reflections h, k, l, m, n, o, p and q on the same intensity scale with the following intensities:

h=100, i=5 to 95, l=1 to 30, m=1 to 40, n=1 to 40, o=1 to 30, p=1 to 30 and q=5 to 60.

6. The process as claimed in any of claims 1 to 5, wherein the stoichiometric coefficients a, b, c and d of the multimetal oxide material M to be washed are simultaneously in the following ranges:

a=from 0.05 to 6;

b=from 0.01 to 1;

c=from 0.01 to 1; and d=from 0.00005 to 0.5.

7. The process as claimed in claim 1, wherein $M^1$=Te.

8. The process as claimed in claim 1, wherein at least 50 mol % of the total amount of $M^2$ is Nb.

9. The process as claimed in claim 1, wherein $M^3$ is at least one element from the group consisting of Ni, Co, Pd and Bi.

10. The process as claimed in claim 1, wherein the preparation of the multimetal oxide material M to be washed is effected by a hydrothermal method.

11. A process for the heterogeneously catalyzed gas-phase partial oxidation and/or animoxidation of a saturated and/or unsaturated hydrocarbon, wherein the catalytically active material used is the direct product of a process as claimed in claim 1.

* * * * *

UNITED STATES PATENT AND TRADEMARK OFFICE
CERTIFICATE OF CORRECTION

| | | |
|---|---|---|
| PATENT NO. | : 7,038,082 B2 | |
| APPLICATION NO. | : 10/647335 | |
| DATED | : May 2, 2006 | |
| INVENTOR(S) | : Frieder Borgmeier et al. | |

It is certified that error appears in the above-identified patent and that said Letters Patent is hereby corrected as shown below:

Column 22, line 22, "K being each $\pm$ 1°" should read -- k being each $\leq$ 1° --.

Column 22, line 55, "35.4 $\cong$ 0.4 ° (n)" should read -- 35.4 $\pm$ 0.4 ° (n) --.

Signed and Sealed this
Twelfth Day of July, 2011

David J. Kappos
*Director of the United States Patent and Trademark Office*